United States Patent [19]

Parthasarathy

[11] Patent Number: 5,262,439
[45] Date of Patent: Nov. 16, 1993

[54] SOLUBLE ANALOGS OF PROBUCOL

[75] Inventor: Sampath Parthasarathy, San Diego, Calif.

[73] Assignee: The Regents of the University of California, Oakland, Calif.

[21] Appl. No.: 876,557

[22] Filed: Apr. 30, 1992

[51] Int. Cl.⁵ ............... A61K 31/225; C07C 69/017; C07C 67/08
[52] U.S. Cl. .................. 514/548; 514/712; 560/138; 562/590; 562/595; 568/52
[58] Field of Search ............ 560/138; 568/52; 514/548, 712; 562/590, 595

[56] References Cited

U.S. PATENT DOCUMENTS

| | | | |
|---|---|---|---|
| 3,576,883 | 4/1971 | Neuworth et al. | 568/52 |
| 3,862,332 | 1/1975 | Barnhart et al. | 514/712 |
| 4,719,237 | 1/1988 | McCaughan | 514/712 |
| 4,985,465 | 1/1991 | Hendler | 514/712 |

OTHER PUBLICATIONS

Daniel Steinberg, (1991), Circulation 84:1420–1425.

Primary Examiner—José G. Dees
Assistant Examiner—Vera C. Clarke
Attorney, Agent, or Firm—Townsend and Townsend Knourie and Crew

[57] ABSTRACT

The invention provides a class of water-soluble probucol derivatives having one or more ester groups replacing the phenyl hydroxyl groups of the probucol molecule. Some derivatives have polar or charged functionalities such as carboxylic acid groups, amino groups, aldehyde groups and amide groups located on the ester groups. Some of these compounds are spontaneously hydrolyzable in typical biological milieus. The present invention also provides method of treating an animal with probucol by administering a water-soluble probucol prodrug to the animal.

14 Claims, No Drawings

SOLUBLE ANALOGS OF PROBUCOL

This invention was made with Government support under Grant No. HL-14197 awarded by the National Institute of Health. The Government has certain rights in this invention.

BACKGROUND OF THE INVENTION

The present invention lies in the field of water-soluble antioxidant formulations. More specifically, the present invention lies in the field of hydrolyzable, water-soluble derivatives of probucol compounds for various applications.

Probucol is a potent antioxidant, chemically related to the widely used food additives 2,[3]-tert-butyl-4-hydroxyanisole (BHA) and 2,6-di-tert-butyl-4-methylphenol (BHT). Probucol and various related compounds have been discussed in various patents including the following: U.S. Pat. No. 3,485,843 issued to Wang, U.S. Pat. No. 3,576,833 issued to Neuworth, U.S. Pat. No. 3,862,332 issued to Barnhart et al., and U.S. Pat. No. 4,985,465 issued to Hendler. Its full chemical name is 4,4'-(isopropylidenedithio) bis(2,6-di-tert-butylphenol), and it has the following structure:

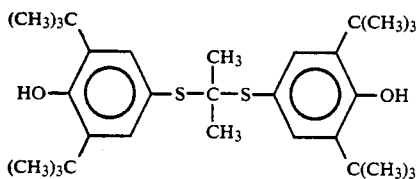

Today, probucol is used primarily to lower serum cholesterol levels in hypercholesterolemic patients, but recent work has shown that it also may be used to treat other ailments such as viral and retroviral infections (e.g. human immunodeficiency virus (HIV-1) infection). The anti-viral properties of probucol are discussed in U.S. Pat. No. 4,985,465, which is incorporated herein by reference for all purposes. Probucol has also been claimed to be effective in treating arrhythmia; see U.S. Pat. No. 4,719,237 issued to McCaughan.

Recent evidence suggests that the atherogenic effects of low density lipoprotein (LDL) may be in part mediated through its oxidative modification. Probucol has been shown to possess potent antioxidant properties and to block oxidative modification of LDL. Consistent with these findings, probucol has been shown to actually slow the progression of atherosclerosis in LDL receptor-deficient rabbits as discussed in Carew et al. Proc. Natl. Acad. Sci. U.S.A. 84:7725–7729 (1987) which is incorporated herein by reference for all purposes. Most likely, probucol is effective because it is highly lipid soluble and is transported by lipoproteins, thus protecting them against oxidative damage.

Unfortunately, probucol is almost insoluble in water and therefore cannot be injected intravenously (it is even difficult for cells to take it up in vitro because of its poor miscibility in buffers and media for cell culture). Thus, probucol is commonly administered in the form of tablets available under the trademark Lorelco TM (Marion Merrell Dow Pharmaceuticals, Inc., Kansas City, Mo.). However, solid probucol is poorly absorbed into the blood, and is excreted in substantially unchanged form. Further, the tablet form of probucol is absorbed at significantly different rates and in different amounts by different patients. In one study (Heeg et al., *Plasma Levels of Probucol in Man After Single and Repeated Oral Doses*, La Nouvelle Presse Medicale, 9:2990–2994 (1980)), peak levels of probucol in sera were found to differ by as much as a factor of 20 from patient to patient. In another study, Kazuya et al. J. Lipid Res. 32; 197–204 (1991) observed an incorporation of less than about 1 $\mu$g of probucol/$10^6$ cells when endothelial cells are incubated for 24 h with 50 $\mu$M probucol.

The low water-solubility of probucol limits its usefulness in another way. When blood flow to a tissue is interrupted and later re-established, there is a so-called reperfusion injury that is largely due to the development of free radicals and consequent oxidative damage. Every year, thousands of patients having myocardial infarctions are injected with thrombolytic agents in an attempt to reopen thrombosed coronary arteries. These patients are at significant risk of developing reperfusion injury. It has been found that anti-oxidants seem to limit post-perfusion injury. In fact, some studies have shown that probucol given orally for some time before tying off a renal artery in the rat can limit the post-perfusion injury in the kidney. Thus, the simultaneous injection of a potent antioxidant might significantly improve the prognosis of such patients. Unfortunately, it takes days to build up probucol levels by oral administration, and it cannot be predicted when someone will have a myocardial infarction.

The above discussion shows that a need exists for a probucol delivery formulation (preferably an aqueous solution) that is readily absorbed by the patient and can be administered intravenously. Unfortunately, known water-soluble antioxidants do not partition into lipoproteins or other membrane lipids where preoxidation occurs. Thus, the desired formulation should also provide an antioxidant that partitions into lipid containing phases.

SUMMARY OF THE INVENTION

The present invention provides a class of water-soluble probucol compounds. These compounds are structurally similar to known probucol compounds, but have ester groups substituted for either or both of the hydroxyl groups located on the bis-phenols. The ester groups are derived from carboxylic acids having a functional group that imparts some increased water-solubility to the highly insoluble probucol compounds. Preferred esters are hydrolyzable to yield a free probucol compound.

In one aspect, the present invention provides a water-soluble derivative of a probucol compound in which at least one phenyl hydroxyl group of the probucol compound is replaced with an ester group having a polar or charged functionality. Upon hydrolysis, the esters of this invention yield the free probucol compound. Preferred compositions of this invention are probucol esters of saturated or unsaturated dicarboxylic acids, amino carboxylic acids, and aldehyde containing carboxylic acids. More preferably, the carboxylic acid groups on the probucol esters of this invention have three to ten carbon atoms.

Particularly preferred esters of probucol compounds have the following formula:

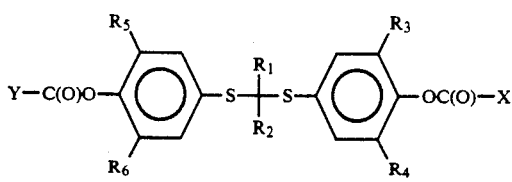

where $R_1$ and $R_2$ independently represent alkyl, alkenyl, or aryl groups of from one to eight carbon atoms inclusive; $R_3$ through $R_6$ independently represent lower alkyl of from one to four carbon atoms inclusive; and X and Y independently represent alkyl or alkenyl groups containing a polar or charged functionality. Preferably, the functionality is a carboxylic acid group, a salt of a carboxylic acid group, an amine group, a salt of an amine group, an amide group, or an aldehyde group.

Preferably, at least two of $R_3$ through $R_6$ represent tert-butyl. More preferably, at least one of $R_3$ and $R_4$ and at least one of $R_5$ and $R_6$ represent tert-butyl. In a specific preferred embodiment, $R_1$ and $R_2$ each represent methyl and $R_3$ through $R_6$ each represent tert-butyl.

In another preferred embodiment, either X or Y, or both X and Y independently represent one to nine carbon atom carboxylic acid groups or carboxylic acid salts. Exemplary salts include salts of alkali metals, alkaline earth metals, ammonia, transition metals, noble metals, heavy metals, etc. Alternatively, X or Y, or both X and Y independently represent one to nine carbon atom alkyl amine groups or alkyl amine salts. Exemplary amine salts include hydrochlorides and quaternary ammonium salts. In another specific embodiment, X and Y represent the same group, preferably —(CH$_2$)$_3$COOH or salts of —(CH$_2$)$_3$COOH.

In another aspect of the present invention, a method is provided for inhibiting oxidation in an animal by administering a pharmaceutically effective dose of a probucol compound ester to the animal. Such compounds may be useful as prodrugs. Suitable prodrugs have hydrolyzable ester groups at the location of the phenyl hydroxyl groups of the probucol compound. Preferred doses of the prodrug are between about 1 and about 50 milligrams per kilogram of body weight depending upon the type and severity of the condition being treated. In some embodiments the pharmaceutical composition is administered intravenously in an aqueous solution. In other embodiments, it is administered orally as a solid or as a an aqueous solution.

In yet another aspect, the present invention provides a method for delivering a therapeutic amount of a probucol compound to a part of an animal that is susceptible to oxidation. The method involves administering a probucol compound ester of the present invention to the animal and then transporting it to the part of the animal being susceptible to oxidation. Finally, the water-soluble derivative is hydrolyzed to release free probucol compound to the part of the animal susceptible to oxidation. Preferably the probucol compound will be released into lipid-containing material in the part of the animal susceptible to oxidation.

A further understanding of the invention can be obtained from the following discussion and accompanying examples.

DESCRIPTION OF THE SPECIFIC EMBODIMENTS

The present invention provides a class of water-soluble compounds which readily hydrolyze into probucol compounds, and can therefore be taken up by lipoproteins or lipid containing substances to prevent peroxidation. Thus, the present invention provides easy to administer and therapeutically effective probucol derivatives that readily convert to potent antioxidants in lipid environments.

As used herein, "probucol compound" refers to probucol or a probucol analog having anti-oxidant properties. Anti-oxidants are generally compounds that scavenge free-radicals capable of causing in vivo and/or in vitro oxidative damage to biological materials. Chemically, probucol is a member of a class of compounds that are sometimes described as sterically hindered phenols, i.e. phenol compounds in which the hydroxyl group on the phenyl ring is at least partially blocked by other groups, such as alkyl groups on adjacent phenyl positions. In many of these compounds, either or both of the ring positions adjacent to the hydroxyl group are substituted with tertiary butyl groups. While not wishing to be bound by theory, it appears that the antioxidant and hypocholesterolemic action of probucol itself requires a chemically free hydroxyl groups.

A preferred group of water-soluble probucol compound derivatives have the following formula:

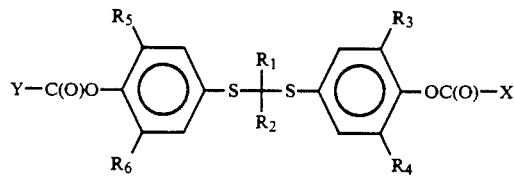

where $R_1$ and $R_2$ independently represent alkyl, alkenyl, or aryl groups of from one to eight carbon atoms inclusive; $R_3$ through $R_6$ independently represent lower alkyl of from one to four carbon atoms inclusive; and X and Y independently represent alkyl or alkenyl groups containing a polar or charged functionality.

In the above structure, the hydroxy position is given the number 1 on each phenyl ring. $R_4$ and $R_5$ are located at the number 2 position, $R_3$ and $R_4$ are located at the number 6 position, and the sulfur atoms attach at the number 4 position. Specific examples of sparingly soluble probucol compounds which can be converted to the water-soluble derivatives of this invention are provided in U.S. Pat. No. 4,985,465 to Hendler, previously incorporated herein by reference. Thus, for example, certain water-soluble derivatives of 4,4'-(isopropylidenedithio) bis(2 tert-butyl, 6-isopropylphenol) are within the class of compounds of the present invention.

In a preferred embodiment, the polar or charged functionality on X and Y is a carboxylic acid group, a salt of a carboxylic acid group, an amine group, a salt of an amine group, an amide group, or an aldehyde group. In a further preferred embodiment, at least two of $R_3$ through $R_6$ represent tert-butyl. More preferably, at least one of $R_3$ and $R_4$ and at least one of $R_5$ and $R_6$ represent tert-butyl. In a specific preferred embodiment, $R_1$ and $R_2$ each represent methyl and $R_3$ through $R_6$ each represent tert-butyl.

In another preferred embodiment, either X or Y, or both X and Y independently represent one to nine carbon atom alkyl or alkenyl groups having a polar or charged functionality. Preferred functionalities include carboxylic acid groups or carboxylic acid salts. Exemplary salts include salts of alkali metals, alkaline earth metals, ammonia, transition metals, noble metals, heavy metals, etc. Alternatively, X or Y, or both X and Y independently represent one to nine carbon atom alkyl amine groups or alkyl amine salts. Exemplary amine salts include hydrochlorides and quaternary ammonium salts. In another specific embodiment, X and Y represent the same group, preferably $(CH_2)_3COOH$ or salts of $(CH_2)_3COOH$.

A particularly preferred embodiment of the present invention is a class of dicarboxylic acid esters of probucol compounds which can be dissolved as sodium or potassium salts. The ester groups of such compounds are readily hydrolyzed, regenerating the biologically active, free probucol compound. For example, the glutaric acid derivative of probucol has been found to hydrolyze in one to three hours in phosphate buffered saline or in Ham's F-10, a cell culture medium.

Among the most preferred dicarboxylic acid esters of probucol compounds are the succinic acid, glutaric acid, adipic acid, suberic acid, sebacic acid, azelaic acid, and maleic acid esters. These compounds may be either the mono or di-esters of the probucol compound. Usually, the diesters are easier to synthesize and are more soluble. Thus, they generally are preferred. In addition, preferred dicarboxylic acid esters are readily convertible into salts such sodium and potassium salts. These salts can be filter-sterilized and then used for both in vitro and in vivo applications. They are particularly useful in preparing probucol at precise concentrations without the need to use organic solvents.

Preferred compounds of this invention will have a solubility in water of greater than about 1 mg/ml. More preferably, they will have a solubility of greater than about 10 mg/ml, and most preferably greater than about 25 mg/ml. Preferably, these compounds will readily hydrolyze in physiological environments to the lipid-soluble probucol compound. Such compounds will be useful in preventing lipid peroxidation or other oxidative damage in vitro or in vivo.

As used herein, "hydrolysis" refers to the conversion of an ester (by saponification) or other compound into an acid and an alcohol by the addition of a water molecule. Often hydrolysis reactions are catalyzed by an excess of acid or base. As used herein, "spontaneous hydrolysis" refers to hydrolysis reactions that occur without the addition of external factors, such as catalysts. For example, if an ester is added to water and is converted to a corresponding carboxylic acid and a corresponding alcohol, the reaction is spontaneous hydrolysis if no catalysts or other external agents are added. Of course, if the ester is added to an already somewhat acidic or basic medium, the hydrolysis is still spontaneous if no additives are required to cause the reaction. In another example, an ester is spontaneously hydrolyzed if it is added to a biological medium and is converted to its constituent acid and alcohol on standing, without addition of other agents Thus, for example, the ester might spontaneously hydrolyze in the blood stream under physiologic conditions. Typically, a spontaneous hydrolysis reaction will occur at an appreciable rate, i.e. the reaction will be complete in a few days or less, and preferably less than about 48 hours.

The water-soluble compounds of the present invention are useful in preventing biological material (especially lipid containing substances) from being oxidatively damaged. Thus, for example, an animal (such as a human) may be treated by administering a pharmaceutically effective dose of a water soluble probucol compound to the animal. Because the compounds of this invention are water soluble, they will, in comparison to traditional probucol compounds, more readily be taken up in the blood stream at higher levels. And because the compounds of this invention have hydrolyzable ester groups, they will convert to the free probucol compounds which can partition lipid containing materials such as lipoproteins. There the probucol compounds will act as a potent antioxidants.

The compositions of the present invention can be administered to humans in daily dosage ranges of preferably about 0.01 to about 100 milligrams per kilogram of body weight, more preferably about 10 to about 50 mg/kg. In the most preferred embodiments, the daily dosage will be about 50 mg/kg. However, this dosage may vary depending upon the severity of the patient's condition and the type of condition being treated. Those of skill in the art will be able to readily determine what dose ranges are appropriate for the particular condition being treated. Thus, different preferred ranges may be appropriate for treatment of arthersclerosis, post-perfusion injury, and viral infections. In addition, the dosage will vary depending upon whether the composition is administered intravenously or orally. Both routes of administration will be useful for particular ailments.

Because the compositions of this invention are water-soluble, they may be transported in aqueous media such as buffers or plasma. Thus, when administered, as by intravenous injection, they are rapidly directed throughout the body to locations that are susceptible to oxidative damage. As these compositions hydrolyze to release free probucol or probucol analog, they are taken up in lipid-containing regions in the animal, including those regions susceptible to oxidation (e.g. plasma membranes and LDL). Cells such as neutrophils and monocytes that undergo rapid respiratory burst upon certain types of stimulation may produce lesser amounts of oxygen radicals when enriched with antioxidants in this manner. Thus leukocytes may generate less superoxide anion radicals when they take up and hydrolyze water-soluble probucol.

The water-soluble compositions of the present invention provide additional benefits for in vitro applications. For example, the salts of these compounds can be filter-sterilized to provide an preservative for plasma, cell cultures and tissue cultures in both clinical and research applications. Such filtered compositions would provide sterile media, capable of preventing peroxidation in lipid-containing materials. In addition, the effects of otherwise insoluble probucol compounds on cells can be more carefully studied because the water-soluble derivatives are more easily taken up by the cells and do not precipitate out of solution when exposed to aqueous solutions (e.g. biological milieus).

The preparation of probucol is well known in the art. For example probucol can be prepared by dissolving 2,6-di-tert-butyl-4-mercaptophenol (47.5 g, 0.2 mol) in methanol (50 ml) heated to 50° C. A catalytic amount of concentrated hydrochloric acid (1 milliliter) is added, followed by acetone (5.8 grams; 0.1 mole). The temperature of the mixture rises to about 60°-65° C. for 1.5 hours. The mixture is cooled, diluted with water and about 10 milliliters of aqueous sodium bicarbonate and extracted with ether. The ether extract is evaporated, and the product is obtained as a residue, which is recrystallized from ethanol and then from isopropanol to obtain probucol as a crystalline solid melting at about 125°–126° C.

In another representative procedure about 2.3 moles of 2,6-di-tert-butyl-4-mercaptophenol is dissolved in about 1700 milliliters of methanol under a nitrogen atmosphere; about 100 milliliters of concentrated hydrochloric acid and 180 milliliters of acetone are added, and the mixture is stirred and maintained at a temperature of about 35°–50° C. for 1 5 hours. The mixture is then cooled to room temperature and filtered, and the probucol is collected as a colorless crystalline solid filler cake. The product is washed with water and aqueous sodium bicarbonate and purified by recrystallization from methanol.

Dicarboxylic acid derivatives of probucol compounds may be prepared according to the following general procedure. The probucol compound is treated with an excess of dicarboxylic acid anhydride and catalytic amounts of 4-dimethyl-aminopyridine at a temperature sufficient to ensure that the dicarboxylic acid anhydride is liquid. Under these conditions, no anhydrous solvent is necessary, as the anhydride itself acts as a solvent. The progress of the reaction is be monitored by chromatography. Substituted monocarboxylic acid probucol esters may be prepared by similar means.

EXAMPLE 1

A water-soluble glutaric acid derivative of probucol was synthesized as follows: probucol was treated with a 40-fold molar excess of glutaric anhydride in the presence of catalytic amounts of 4-dimethyl-aminopyridine at 130° C. for 24 hours. The formation of probucol diglutarate was monitored by thin layer chromatography (TLC) (n-hexane:diethyl ether:acetic acid, 70:30:1 vol/vol/vol). The product was purified by silicic acid column chromatography using increasing amounts of ether in hexane. The purified product gave a single spot on TLC (Rf 0.18) distinct from the parent compound (Rf 0.68). Upon alkaline hydrolysis, the compound yielded free probucol. In its acid form, the diglutarate is soluble in organic solvents, and, upon removal of the solvent, can be dissolved in sodium bicarbonate solution. The resulting solution can be put through a 0.45-μM filter to ensure sterility and to remove any free probucol. The sodium salt in aqueous solution undergoes slow hydrolysis yielding free probucol.

In another synthesis, probucol (1 mMol) was weighed in a clean, dry 25 ml Erlenmeyer flask. 5 μmMol of 4-dimethylaminopyridine was added as catalyst. 15 mMols of glutaric anhydride was then added and the flask was heated to 175° C. for 8 hours. (Preliminary studies showed that at this ratio of probucol to anhydride, the reaction is about 75% complete in 1 hour). The flask was then cooled and the sample was dissolved in 10 ml of 1:1 hexane:diethylether. The reaction was checked by thin layer chromatography using silica gel 1B-F (J. T. Baker) and the solvent system hexane:ether (70/30 V/V). Free probucol had the highest mobility (0.5–0.6), and the probucol ester remained close to the origin with an Rf of about 0.1–0.15. The entire reaction mixture (after concentration) was applied to a silica gel column (40 cm×2 cm) and eluted with increasing concentrations of ether or hexane. The fractions were monitored by TLC. Pure fractions were collected and concentrated. The compound was rechecked by TLC. The reaction yield was approximately 75%.

The sample released free probucol when saponified with an alkali and subjected to ether extraction. Because of this and because the derivatives are soluble in aqueous sodium bicarbonate, the following sequence of reaction is likely (although not critical to the present invention).

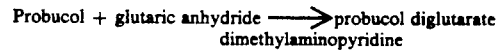

Probucol + glutaric anhydride ⟶ probucol diglutarate
dimethylaminopyridine

The absence of a monoester is suggested by the lack of intermediate in TLC even at lower concentrations of the anhydride. Dimethylaminopyridine has been used as a catalyst in esterification of fatty acid anhydrides in other lipid syntheses. An important feature of the present method is the use of the molten anhydride itself as the solvent, thus avoiding the need for anhydrous solvents. Although the above examples pertained to the glutaric acid derivative of probucol, other anhydrides can also be used in place of glutaric anhydride depending on the derivative desired. For example, maleic anhydride can be used (at a much lower temperature than the glutanic anhydride reaction) to produce probucol dimaleate.

EXAMPLE 2

The effect of preincubation with 500 nmol/ml of probucol (added in ethyl alcohol) on the ability of macrophages to oxidize LDL is shown in Table I. Mouse peritoneal macrophages ($3 \times 10^6$ cells per dish in a 6 well plate) were treated with 500 nmol probucol in 1 ml of DME containing 5 mg/ml lipoprotein deficient serum. Probucol was added in 10 μl ethanol. After 48 hours the cells were washed 3 times with 3 ml of Ham's F-10 and then subjected to incubation with $^{125}$I-LDL (1100 μg/ml) in 2 ml of Ham's F-10 for 20 hours. TBARS and subsequent macrophage degradation were determined. The results are averages from a triplicate determination from a representative set.

TABLE 1

| | TBARS nmol/mg protein | Macrophage degradation μg/5 h per mg cell protein |
|---|---|---|
| Native LDL | 2.6 | 1.1 |
| LDL incubated with control macrophages | 48.4 | 6.7 |
| LDL incubated with probucol-pretreated macrophages | 11.2 | 2.1 |

Probucol itself has a very limited solubility and the medium in these studies was grossly milky. After several washings with Ham's F-10, the cells were then incubated with 200 μg of $^{125}$I-LDL in 2 ml. of Ham's F-10 for 24 hours. As seen in the table, the cells that were incubated with probucol modified LDL poorly as compared to control cells not pretreated with probucol. This suggested that antioxidant enrichment of the cells might afford additional protection for LDL against cell-catalyzed oxidation. However, because the probucol was obviously not in solution and might remain absorbed to the cell surface even after washing, it is possible that residual probucol on the cell surface accounted for the apparent protection during the second incubation, i.e., probucol from the cell surface might transfer into the LDL during the first part of the second incubation. To remove this possibility, the water-soluble probucol analogue, diglutaryl probucol, synthesized as described in Example 1 was prepared for study.

Oxidative modification of LDL was strongly inhibited by even very low concentrations of diglutaryl probucol (more than 50% at 2.5 μM), but it was found that the diglutaryl probucol had been almost completely hydrolyzed in the course of the 24 hour incubation, i.e., the medium at the end of incubation contained exclusively probucol itself. Thus it was not possible to determine to what extent the observed inhibition reflected the uptake of diglutaryl probucol into the cells, on the one hand, and the effects of free probucol generated by hydrolysis of the diglutaryl derivative during the incubation, on the other. Similar experiments were done using copper-induced oxidation and with similar results (data not shown).

In the next series of studies, endothelial cells (EC) and mouse peritoneal macrophages (Mφ) were incubated with diglutaryl probucol (sodium salt) or probucol (in ethanol) for only a short period of time (3 hours at 37° C.) to limit the extent of spontaneous hydrolysis. Then the cells were thoroughly washed to remove any extracellular inhibitors. Specifically, they were washed three times with 3 ml of F-10 containing 10% fetal calf serum and then incubated with labeled LDL for an additional 24 hours. As shown in Table 2, the pretreated cells were strongly inhibited with respect to their ability to induce LDL oxidation, measured either in terms of thiobarbituric acid reactive material or in terms of the biological modification (i.e., the increase in the rate of subsequent LDL degradation in 5 hour incubation with macrophages). Concentrations as low as 10 μM diglutaryl probucol inhibited the modification completely. The values given are from a typical experiment from three or more separate experiments.

TABLE 2

|  | TBARS nmol/mg protein | Macrophage degradation μg/5 h per mg cell protein |
| --- | --- | --- |
| Set A |  |  |
| Native LDL | 5.5 | 1.6 |
| LDL incubated with: |  |  |
| Control EC | 52.5 | 7.2 |
| EC pretreated with 25 μM diglutaryl probucol | 12.1 | 1.5 |
| 50 μM diglutaryl probucol | 6.5 | 1.3 |
| 100 μM probucol | 42.5 | 6.4 |
| Set B |  |  |
| Native LDL | 3.2 | 1.5 |
| LDL incubated with: |  |  |
| Control macrophages | 21.8 | 5.5 |
| Macrophages pretreated with: |  |  |
| 10 μM diglutaryl probucol | 5.3 | 2.2 |
| 20 μM diglutaryl probucol | 4.1 | 1.6 |
| 30 μM diglutaryl probucol | 3.3 | 1.4 |

TABLE 2-continued

|  | TBARS nmol/mg protein | Macrophage degradation μg/5 h per mg cell protein |
| --- | --- | --- |
| probucol |  |  |

The uptake of probucol glutarate by endothelial cells and macrophages was studied by using $^{14}$C-labeled water-soluble derivative. The sodium salt of $^{14}$C-diglutaryl probucol was added to washed cells at the specified concentrations and incubated in 1 ml of DME medium for 37° C. for 3 hours. The cells were then washed three times with DME. (The medium after the last washing did not contain any radioactivity). The cells were dissolved in 1 ml of 0.01% Triton X-100 before the determination of radioactivity. Values for macrophages represent averages of duplicate determinations from one of two separate trials. Values for endothelial cells are from four individual cell incubations.

More than 96% of the labeled derivative readily went into the solution as the sodium salt and when incubated with macrophages was effectively taken up by the cells. About 25-30% of the added radioactivity (2.5-6.5 nmol of probucol/~40 μg of cell protein) was associated with the cells after 2 hours (Table 3). At 60 minutes about half of the cell associated with radioactivity was in the form of the precursor, probucol diglutarate.

TABLE 3

| Cell Type | Nmol $^{14}$C-diglutaryl | Nmol of cell Associated $^{14}$C-Radioactivity |
| --- | --- | --- |
| Macrophages | 5 | 2.5 |
|  | 10 | 3.7 |
|  | 15 | 4.2 |
|  | 20 | 5.2 |
|  | 25 | 6.5 |
| Endothelial cells | 5 | 1.9 ± 0.14 |

It was still necessary to consider the possibility that free probucol generated during the 3 hour incubation or generated by hydrolysis in the cell might find its way into the LDL particle and act as an antioxidant in the medium. Thus, endothelial cells were incubated with 25 nmol of $^{14}$C-labeled diglutaryl probucol for 3 hours and after washing fresh medium and LDL were added. The LDL recovered from the medium showed absence of oxidation but was readily modified upon a subsequent incubation in the presence of 5 μM copper. However, when higher concentrations 50-200 nmol of diglutaryl probucol were incubated with endothelial cells, there was considerable release of free probucol into the medium (in a 24 hour incubation) even after several washings with medium containing lipoprotein-deficient medium. Nevertheless, after two subsequent incubations with LDL at 100 μg/ml for 24 hours each, 30-45% of the incorporated radioactivity was still associated with the cells. It should be pointed out that in these experiments, more than 15 nmol of probucol was incorporated into the cells of which about 7 nmol were released into the medium during a 24 hour incubation with LDL. The LDL recovered from such incubations was resistant to modification upon a subsequent incubation with 5 μM copper. Thus, cells enriched in probucol, also released the antioxidant into the medium which may offer additional protection against oxidation. The rate of release of probucol from cells was not followed in these studies.

While the presence of probucol in LDL clearly protects it to some extent against oxidative modification, by acting as a relatively nonspecific antioxidant within the LDL particle, the present results suggest an additional mode of action that may be relevant to the in vivo effects of probucol. While the rate of entrance of probucol into cells in culture is slow, the cells of animals treated chronically with the drug may take up enough of it so that their metabolism is altered, most specifically, their ability to oxidatively modify LDL. Probucol has been reported to accumulate in several tissues at concentrations even higher than in plasma. Other studies have implicated lipoxygenases in the oxidative modification of LDL. It has been proposed that the lipoxygenases act initially on cell lipids to generate hydroperoxides of fatty acids which are then transferred to the LDL. Probucol within the cell might prevent the generation of such lipoperoxides either by acting directly on the lipoxygenase systems or by limiting propagation reactions within the cell membrane. Cells may also release stored probucol into the extracellular medium, thus limiting lipid peroxidation. These findings suggest still another strategy for inhibition of oxidative modification of LDL, i.e., the introduction of compounds into cells to inhibit their ability to induce LDL oxidation. The combination of an antioxidant within the LDL molecule and the presence of an inhibitor within the cells might be additive. Thus, the antiatherogenic effects of probucol may very well depend upon such a two-pronged mode of action.

In summary, the probucol compound derivatives of this invention offer a convenient, water-soluble, filter-sterilizable means of delivering a pro-drug that is efficiently taken up by cells and releases free probucol upon hydrolysis.

Although the above discussion has focused on certain preferred embodiments of the present invention, some variations of the compositions and methods will be apparent to those skilled in the art. For example, the probucol formulations of the present invention could be employed to treat conditions in a variety of mammals other than humans. Further, the compounds of this invention could be prepared using anhydrous solvents capable of dissolving the anhydride and probucol compound reactants. These and other modifications are intended to be included with the scope of the claims appended hereto.

What is claimed is:

1. A composition of matter comprising a water-soluble derivative of a sparingly soluble probucol compound having a pair of phenyl hydroxy groups, the water-soluble derivative having ester substitutions at either or both of the phenyl hydroxyl groups, said water-soluble derivative yielding the probucol compound upon hydrolysis and wherein said water-soluble derivative is selected from the group consisting of succinic acid esters, glutaric acid esters, adipic acid esters, suberic acid esters, sebacic acid esters, azelaic acid esters, and maleic acid esters.

2. A composition of matter comprising a water-soluble derivative of a sparingly soluble probucol compound having a pair of phenyl hydroxy groups, the water-soluble derivative having ester substitutions at either or both of the phenyl hydroxyl groups, wherein said water-soluble derivative of probucol spontaneously hydrolyzes under physiologic conditions in the blood stream yielding the probucol compound.

3. A composition of matter comprising a water-soluble derivative of a sparingly soluble probucol compound having a pair of phenyl hydroxy groups, the water-soluble derivative having ester substitutions at either or both of the phenyl hydroxyl groups, said water-soluble derivative yielding the probucol compound upon hydrolysis, wherein said water-soluble derivative of probucol has a solubility in water of greater than about 1 mg/ml.

4. A composition of matter having the following formula:

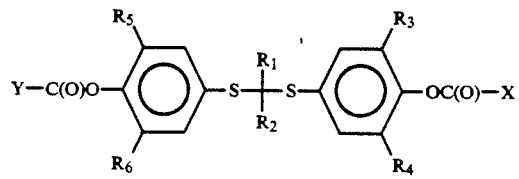

wherein $R_1$ and $R_2$ independently represent alkyl, alkenyl, or aryl groups of from one to eight carbon atoms inclusive; $R_3$ through $R_6$ independently represent lower alkyl of from one to four carbon atoms inclusive, of which at least two of the groups $R_3$ through $R_6$ represent tert-butyl groups; and X and Y independently represent alkyl or alkenyl groups containing a functionality selected from the group consisting of carboxylic acid groups, salts of carboxylic acid groups, amine groups, salts of amine groups, amide groups, and aldehyde groups.

5. The composition of claim 4 wherein at least one of $R_3$ and $R_4$ represents tert-butyl and at least one of $R_5$ and $R_6$ represents tert-butyl.

6. The composition of claim 4 wherein $R_1$ and $R_2$ each represent methyl and wherein $R_3$ through $R_6$ each represent tert-butyl.

7. A composition of matter having the following formula:

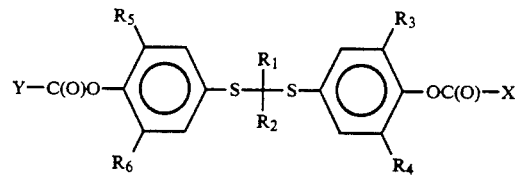

wherein $R_1$ and $R_2$ independently represent methyl or ethyl groups; $R_3$ through $R_6$ independently represent lower alkyl of from one to four carbon atoms inclusive; and X and Y independently represent alkyl or alkenyl groups containing a functionality selected from the group consisting of carboxylic acid groups, salts of carboxylic acid groups, amine groups, salts of amine groups, amide groups, and aldehyde groups.

8. A composition of matter having the following formula:

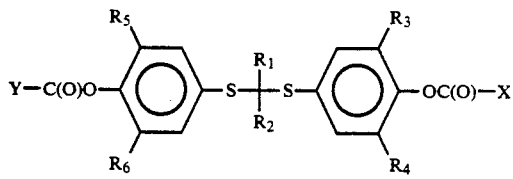

wherein $R_1$ and $R_2$ independently represent alkyl, alkenyl, or aryl groups of from one to eight carbon atoms inclusive; $R_3$ through $R_6$ independently represent lower alkyl of from one to four carbon atoms inclusive; and X and Y independently represent one to nine carbon atom carboxylic acid groups.

9. A composition of matter having the following formula:

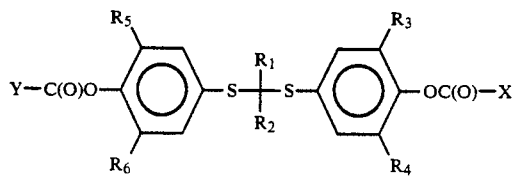

wherein $R_1$ and $R_2$ independently represent alkyl, alkenyl, or aryl groups of from one to eight carbon atoms inclusive; $R_3$ through $R_6$ independently represent lower alkyl of from one to four carbon atoms inclusive; and X and Y represent the same alkyl or alkenyl group containing a functionality selected from the group consisting of carboxylic acid groups, salts of carboxylic acid groups, amine groups, salts of amine groups, amide groups, and aldehyde groups.

10. A method for treating an oxidation related condition in an animal by administering to said animal a pharmaceutically effective does of a probucol compound prodrug, wherein said prodrug is administered in a dose of between about 0.01 and about 50 milligrams per kilogram of body weight of the animal, said prodrug having hydrolyzable ester substitutes at either or both of the phenyl hydroxyl groups of the probucol compound.

11. A method for treating an oxidation related condition in an animal by administering intravenously in an aqueous solution to said animal, a pharmaceutically effective dose of a probucol compound prodrug, said prodrug having hydrolyzable ester substitutes at either or both of the phenyl hydroxy groups of the probucol compound.

12. A method for treating an oxidation related condition in an animal by administering orally to said animal a pharmaceutically effective dose of a probucol compound prodrug, said prodrug having hydrolyzable ester substitutes at either or both of the phenyl hydroxyl groups of the probucol compound.

13. A method of delivering a therapeutic amount of probucol or a probucol analog to part of an animal, said part being susceptible to oxidation, said method comprising the following steps:
  administering a water-soluble ester of probucol or a probucol analog to said animal; and
  hydrolyzing said ester to release free probucol or probucol analog, said hydrolyzing action occurring at the part of said animal susceptible to oxidation, wherein the free probucol or probucol analog is released into a lipid containing material.

14. A method for preparing a water-soluble derivative of a probucol compound, the method comprising the following steps:
  preparing a solution of the probucol compound and a carboxylic acid anhydride containing a polar or charged functionality, wherein said carboxylic acid anhydride is selected from the group consisting of succinic acid anhydride, glutaric acid anhydride, adipic acid anhydride, suberic acid anhydride, sebacic acid anhydride, azelaic acid anhydride, and maleic acid anhydride; and
  adding a catalyst for the esterification reaction of the probucol compound to said solution.

* * * * *